United States Patent
Strobel et al.

(10) Patent No.: US 11,295,852 B2
(45) Date of Patent: Apr. 5, 2022

(54) PERSONALIZED PATIENT MODEL

(71) Applicant: Siemens Healthcare GmbH, Erlangen (DE)

(72) Inventors: Norbert Strobel, Forchheim (DE); Xia Zhong, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 643 days.

(21) Appl. No.: 16/135,168

(22) Filed: Sep. 19, 2018

(65) Prior Publication Data

US 2019/0096520 A1 Mar. 28, 2019

(30) Foreign Application Priority Data

Sep. 28, 2017 (EP) .................................... 17193766

(51) Int. Cl.
*G16H 30/20* (2018.01)
*G16H 50/50* (2018.01)
(Continued)

(52) U.S. Cl.
CPC ............. *G16H 30/20* (2018.01); *G06T 7/149* (2017.01); *G06T 7/344* (2017.01); *G06T 19/20* (2013.01);
(Continued)

(58) Field of Classification Search
None
See application file for complete search history.

(56) References Cited

U.S. PATENT DOCUMENTS

| 5,740,802 A * | 4/1998 | Nafis | G16H 50/50 600/407 |
| 6,236,878 B1 * | 5/2001 | Taylor | G16H 50/50 600/416 |

(Continued)

OTHER PUBLICATIONS

Schaller, Christian et al. "Inverse C-arm positioning for interventional procedures using real-time body part detection" Medical Image Computing and Computer-Assisted Intervention—MICCAI 2009: 12th International Conference, London, UK, Sep. 20-24, 2009, Proceedings, Part I (pp. 549-556); DOI: doi.org/10.1007/978-3-642-04268-3_68.

(Continued)

*Primary Examiner* — Oneal R Mistry
*Assistant Examiner* — Nicolas James Boyajian
(74) *Attorney, Agent, or Firm* — Harness, Dickey & Pierce, P.L.C.

(57) ABSTRACT

A method is for calculating a personalized patient model including an external surface model of a patient and an organ model of the patient. In an embodiment, the method includes acquiring metadata of the patient, the metadata being assigned to at least one metadata category; ascertaining, using the patient metadata acquired, the external surface model of the patient and an internal anatomical model of the patient, the internal anatomical model including a body cavity of the patient; ascertaining the organ model of the patient using the patient metadata acquired and using the internal anatomical model of the patient ascertained; and calculating the personalized patient model, the external surface model of the patient ascertained and the organ model of the patient ascertained, being combined.

21 Claims, 4 Drawing Sheets

(51) Int. Cl.
  G06T 19/20    (2011.01)
  G06T 7/33     (2017.01)
  G06T 7/149    (2017.01)
  G06F 3/0484   (2013.01)
  G16H 10/60    (2018.01)
  G06N 20/00    (2019.01)
  G06F 16/50    (2019.01)

(52) U.S. Cl.
  CPC .......... *G16H 50/50* (2018.01); *G06F 3/0484* (2013.01); *G06F 16/50* (2019.01); *G06N 20/00* (2019.01); *G06T 2219/2004* (2013.01); *G16H 10/60* (2018.01)

(56) References Cited

U.S. PATENT DOCUMENTS

| | | | | |
|---|---|---|---|---|
| 2012/0097178 | A1* | 4/2012 | Helm | A61B 6/482 128/898 |
| 2012/0197619 | A1* | 8/2012 | Namer Yelin | G16H 50/50 703/11 |
| 2016/0092748 | A1* | 3/2016 | Koktava | G06K 9/6201 382/128 |
| 2016/0306924 | A1* | 10/2016 | Singh | G16H 30/20 |
| 2017/0249423 | A1* | 8/2017 | Wang | G16H 30/20 |

OTHER PUBLICATIONS

Ding, Aiping et al. "Extension of RPI—adult male and female computational phantoms to obese patients and a Monte Carlo study of the effect on CT imaging dose" Physics in Medicine & Biology; vol. 57; No. 9; pp. 2441-2459; 2012; doi: 10.1088/0031-9155/57/9/2441.

Na, Yong Hum et al. "Mesh-Based and Anatomically Adjustable Adult Phantoms and a Case Study in Virtual Calibration of a Lung Counter for Female Workers" Handbook of Anatomical Models for Radiation Dosimetry; CRC Press, pp. 347-375, 2009; XP055456353; ISSN: 0031-9155 ; ISBN: 9781420059809; / Sep. 1, 2009.

Johnson, Perry B. et al. "Skin dose mapping for fluoroscopically guided interventions" Medical Physics; vol. 38; No. 10; pp. 5490-5499; Oct. 2011; doi: 10.1118/1.3633935.

Xu, X George "An exponential growth of computational phantom research in radiation protection, imaging, and radiotherapy: a review of the fifty-year history" Physics in Medicine and Biology, Institute of Physics Publishing, Bristol GB, vol. 59, No. 18, pp. 233-302, 2014; XP020270227, ISSN: 0031-9155, DOI:10.1088/0031-9155/59/18/R233 / Aug. 21, 2014.

Na, Yong Hum et al. "Deformable adult human phantoms for radiation protection dosimetry: anthropometric data representing size distributions of adult worker populations and software algorithms" Physics in Medicine and Biology, Institute of Physics Publishing, Bristol GB, vol. 55, No. 13, pp. 3789-3811, 2010; XP020193986; ISSN: 0031-9155, DOI: 10.1088/0031-9155/55/13/015/ Jun. 15, 2010.

Avants, B. B. et al. "Symmetric diffeomorphic image registration with cross-correlation: Evaluating automated labeling of elderly and neurodegenerative brain" Medical Image Analysis, ELSEVIER, vol. 12, pp. 26-41, 2008.

European Search Report for 17193766.7 dated Mar. 22, 2018.

Alziar, I. et al. "Individual radiation therapy patient whole-body phantoms for peripheral dose evaluations: method and specific software" Physics in Medicine & Biology, vol. 54, No. 17, Aug. 4, 2009 //https://iopscience.iop.org/article/10.1088/0031-9155/54/17/N01/meta.

European Office Action dated Sep. 15, 2020.

X. Zhong et al: "Generation of Personalized Computational Phantoms Using Only Patient Metadata"; IEEE Nuclear Science Symposium and Medical Imaging Conference 2017; Dec. 31, 2017 ; XP055455199.

European Office Action dated Apr. 8, 2019.

* cited by examiner

PERSONALIZED PATIENT MODEL

PRIORITY STATEMENT

The present application hereby claims priority under 35 U.S.C. § 119 to European patent application number EP17193766.7 filed Sep. 28, 2017, the entire contents of which are hereby incorporated herein by reference.

FIELD

Embodiments of the invention generally relate to a method for calculating a personalized patient model, an associated computing unit and an associated computer program product.

BACKGROUND

Personalized patient models, which, for example, map a surface model of a patient or an anatomical model of the patient, are used in a plurality of medical applications.

For example, during a diagnostic imaging examination of a patient, for example in a computed tomography scanner, the surface model of the patient is acquired with a depth camera and the surface model of the patient is used to improve the positioning of the patient. US 2016/0306924 A1 to Singh et. al, the entire contents of which are incorporated herein by reference, discloses a method for estimating a surface model of a patient by use of a depth camera.

Typically, a personalized patient model is used for the continuous observation of dosimetry scores, for example a patient skin dose ("peak skin dose") or to improve system settings during an imaging examination. A further field of application is, for example, relative positioning of an X-ray based C-arm system with respect to the patient. The personalized patient model is in particular defined without reference to a specific anatomy or morphology of the respective patient, but only based on empirical values, for example from a large patient collective and/or textbooks.

In many applications, personalized patient models are adapted in accordance with a body-mass index. For example, a personalized patient model, which was especially calculated for a first patient or is defined in a textbook, is adapted in accordance with the body mass index of a second patient. Usually, a fat content of the surface model of the personalized patient model of the first patient is scaled as a function of the body mass index of the second patient.

SUMMARY

In other words, in these applications, only the circumference of the surface model of the personalized patient model of the first patient is changed and no individual personalized patient model is calculated for the second patient. The inventors have recognized that, in these cases, the anatomical models are often left unchanged, which represents a severe restriction since the body mass index usually has an influence on the patient's anatomy and morphology.

At least one embodiment of the invention is directed to disclosing a robust method for calculating a personalized patient model with only a few input parameters.

Advantageous embodiments are described in the claims.

The method according to at least one embodiment of the invention is for calculating a personalized patient model including an external surface model of a patient and an organ model of the patient, the method comprising:

acquiring metadata of the patient, the metadata being assigned to at least one metadata category;

ascertaining, using the patient metadata acquired, the external surface model of the patient and an internal anatomical model of the patient, the internal anatomical model including a body cavity of the patient;

ascertaining the organ model of the patient using the patient metadata acquired and using the internal anatomical model of the patient ascertained; and calculating the personalized patient model, the external surface model of the patient ascertained and the organ model of the patient ascertained, being combined.

The computing unit according to at least one embodiment of the invention for the calculation of the personalized patient model comprises a computing module. The computing unit is in particular embodied to calculate the personalized patient model. The computing module in particular comprises a processor and a working memory, wherein the processor can preferably carry out the method steps for calculating the personalized patient model. The computing unit can additionally comprise an input device and the screen, wherein, for example, the user can acquire the patient metadata via the input device and in particular display this on the screen. Preferably, the screen can display the personalized patient model and/or stored it on a hard disk of the computing unit.

The computing unit according to at least one embodiment of the invention for calculating a personalized patient model, comprises a computing module embodied to carry out at least
    acquiring metadata of the patient, the metadata being assigned to at least one metadata category;
    ascertaining, using the patient metadata acquired, the external surface model of the patient and an internal anatomical model of the patient, the internal anatomical model including a body cavity of the patient;
    ascertaining the organ model of the patient using the patient metadata acquired and using the internal anatomical model of the patient ascertained; and
    calculating the personalized patient model, the external surface model of the patient ascertained and the organ model of the patient ascertained, being combined.

The computing unit can, for example, transfer the personalized patient model and/or the patient metadata via a suitable interface to a computer network or to the medical imaging device or to an external memory unit and/or retrieve them therefrom. The computing unit is preferably connected to the computer network, in particular the surface model database and/or the medical image database. Alternatively or additionally, the computing unit or the external memory unit connected to the computing unit can comprise the surface model database and/or the medical image database. The computing unit can in particular comprise the model generator and/or the organ-model generator.

The computer program product according to at least one embodiment of the invention, which can be loaded directly into a memory of a programmable computing unit, comprises program code segments for carrying out a method of an embodiment, when the computer program product is executed in the computing unit. The computer program product can be a computer program or comprise a computer program. This enables the method according to an embodiment of the invention to be carried out in a rapid, identically repeatable and robust manner.

The computer program product is preferably configured such that it can carry out the methods steps according to an embodiment of the invention via the computing unit. The computer program product is, for example, stored on a non-transitory computer-readable medium or held in the computer network or on a server from where it can be loaded into the processor of the computing unit. Furthermore, control information of the computer program product can be stored on an electronically readable data carrier. The control information of the electronically readable data carriers can be embodied such it carries out a method according to the invention that when the data carrier is used in the computing unit. Thus, the computer program product can also depict the electronically readable data carrier.

Examples of electronically readable data carriers are a DVD, a magnetic tape, a hard disk or a USB stick on which electronically readable control information, which in particular correspond to program code segments are stored. When this control information is read from the data carrier and stored in the computing unit, all the inventive embodiments of the above-described method can be performed. For example, at least one embodiment of the invention can also be based on the computer-readable medium and/or the electronically readable data carrier. The computer program product can in particular comprise the model generator and/or the organ-model generator.

BRIEF DESCRIPTION OF THE DRAWINGS

Further features, advantages or alternative embodiments of the method according to the invention for the calculation of the personalized patient model and/or the associated computing unit and/or the associated computer program product can also be transferred to the respective other claimed subject matter and vice versa.

The following describes and explains the invention in more detail with reference to the example embodiments depicted in the figures, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to at least one embodiment of the invention is for calculating a personalized patient model including an external surface model of a patient and an organ model of the patient, the method comprising:

acquiring metadata of the patient, the metadata being assigned to at least one metadata category;

ascertaining, using the patient metadata acquired, the external surface model of the patient and an internal anatomical model of the patient, the internal anatomical model including a body cavity of the patient;

ascertaining the organ model of the patient using the patient metadata acquired and using the internal anatomical model of the patient ascertained; and calculating the personalized patient model, the external surface model of the patient ascertained and the organ model of the patient ascertained, being combined.

The personalized patient model, in an embodiment, comprises a computer-based, typically digital, copy of the patient. The personalized patient model can preferably be calculated individually for the patient in accordance with the patient metadata. The personalized patient model can typically be referred to as a computer-based phantom. The external surface model in particular comprises a digital representation of the surface of the patient. The surface of the patient can, for example, correspond to the skin of the patient. The organ model of the patient in particular comprises one of the patient's organs, for example a heart, a lung, a spleen, a kidney or a liver. The organ model can in particular comprise a plurality of organs, such as, for example, the heart and the liver. The organ model in particular comprises a position and/or a volume of the respective organ.

The external surface model, the internal anatomical model and the organ model can in each case be depicted as image-based or as mathematically modeled, for example. Further depictions or representations are conceivable. An image-based, in particular voxel-based, depiction corresponds, for example, to a recording with an optical camera or in a diagnostic image device. A mathematically modeled depiction can correspond to a mathematical model, a grid, polygons, volumes and/or a set of coordinates. Preferably, it is, for example, possible for an image-based depiction of the organ model to be converted into a mathematically modeled depiction and vice versa.

The patient metadata is, for example, acquired by a user or a physician. The metadata is in particular anyway collected from the patient in the context of a patient questionnaire or is, for example, already included in the patient's medical records. For example, the user can obtain the metadata by questioning the patient and/or retrieve it from medical records. The metadata in particular comprises data describing the patient. The metadata can, for example, be measured by the user. The metadata can in particular be available in the patient's medical records and also provided in a suitable format, for example a DICOM format (Digital Imaging and Communications in Medicine). Typically, the metadata does not include the personalized patient model.

The at least one metadata category, in an embodiment, enables the respective assigned metadata to be sorted and compared. The at least one metadata category can be part of a standard, for example selected in accordance with the DICOM format, or, on the other hand, can be selected more or less in free-text format.

The body cavity of the patient, in an embodiment, corresponds to free space inside the patient. Alternatively or additionally, the body cavity can comprise the organ, for example the heart. Preferably, the body cavity can comprise a plurality of organs, for example the heart and the lung. In other words, in this case, the organ, for example the heart and the lung, can be arranged within the body cavity. In other words, the body cavity can also be referred to as an anatomical enclosure or convex enclosure.

The internal anatomical model, in an embodiment, includes a depiction of the body cavity of the patient. In particular, the internal anatomical model corresponds to this depiction. The internal anatomical model of the patient and the organ model of the patient in particular differ from the surface model in that in each case they comprise the structure, internal morphology and/or anatomy of the patient, while the surface model describes the external morphology and/or anatomy of the patient. Herein, it is typically not possible to acquire the internal morphology and/or anatomy from the exterior of the patient by way of the human eye. On the other hand, it is typically possible to acquire the external morphology and/or anatomy of the patient by way of the human eye.

Preferably, patient metadata is used as the input parameters used for the ascertainment of the external surface model of the patient and the internal anatomical model of the patient. In this case, preferably only patient metadata parameters are used as the input parameters. For example, it is possible to use a model generator, which is embodied or trained to ascertain the external surface model of the patient and the internal anatomical model of the patient. The external surface model of the patient and the internal anatomical model of the patient are in particular output data of the model generator when the patient metadata is used as the input parameters. In this case, the patient metadata in particular entails the inputs parameters of the model generator. The model generator can access further data, which typically are not assigned to the patient. The further data can comprise medical image datasets and/or camera images. Typically, the further data is not acquired by the user or the physician.

The patient metadata and the internal anatomical model of the patient are preferably used as input parameters for the ascertainment of the organ model. Typically, herein, the patient metadata and the internal anatomical model of the patient are the only input parameters assigned to the patient. For example, the model generator, which is embodied to ascertain the external surface model of the patient and the internal anatomical model of the patient, or a further organ-model generator can be embodied and/or trained to ascertain the organ model of the patient. In this case, in particular output data of the model generator and/or the organ-model generator can comprise the organ model when the patient metadata and the internal anatomical model of the patient are used as the input parameters. In this case, the patient metadata and the internal anatomical model of the patient are in particular the input parameters of the model generator and/or the organ-model generator.

The model generator and/or the surface-model generator can be trained in a training phase. The training phase can, for example, be performed by a manufacturer of the model generator and/or the surface-model generator or by the user. During the training phase, usually, a relationship between the at least one metadata category and the external surface model of the patient, the internal anatomical model of the patient and/or the organ model of the patient is determined. In an application phase, in particular the personalized patient model is calculated in accordance with the patient metaparameters.

Combination of the external surface model of the patient and the organ model of the patient can, for example, mean that a coordinate system of the external surface model and a coordinate system of the organ model are matched to one another. Matching means joining the external surface model of the patient and the organ model of the patient relative to the respective coordinate system. Alternatively or additionally, the external surface model of the patient and the organ model of the patient can be correlated to one another, wherein the relationship is retained during the ascertainment of the external surface model of the patient, the internal anatomical model of the patient and the organ model of the patient.

The calculated personalized patient model is in particular made available, for example displayed on a screen and/or stored in a database. The personalized patient model is in particular made available for an application.

The personalized patient model can be used in at least one of the following applications:

positioning of the patient in accordance with the personalized patient model for an imaging examination or a therapy session, avoidance of collisions between a medical imaging device or therapeutic device and the patient in accordance with information in the personalized patient model, calculation of a dose distribution in particular on the skin ("peak skin dose") and/or inside the patient ("organ dose, equivalent patient dose") in accordance with the personalized patient model during the imaging examination or the therapy session, calculation of a dose distribution in an examination room, in which, for example, the medical imaging device or therapeutic device is arranged, in accordance with the personalized patient model, wherein in particular the dose distribution is calculated for the physician or the user ("staff dose"), automatic positioning of the medical imaging device or the therapeutic device in accordance with the personalized patient model, in particular during the imaging examination or the therapy session, for example for a posterior-anterior recording of the patient's heart via an X-ray-based C-arm system or an angiography system, optimization of a scan parameter of the medical imaging device, in particular a tube current and/or a tube voltage of the X-ray-based C-arm system, in accordance with the personalized patient model in respect of an optimum dose and/or image quality, in particular in dependence on an angulation of the X-ray-based C-arm system.

Therefore, the method according to the invention, in at least one embodiment, for the calculation of the personalized patient model in particular has at least one of the following advantages: the personalized patient model is in particular calculated solely based on patient metadata as input parameters. The multi-step approach, for example, first, calculation of the internal anatomical model and subsequent calculation of the organ model, usually enables a particularly robust calculation of the personalized patient model. The personalized patient model in particular comprises the external surface model and the organ model which are calculated solely using the patient metadata. The personalized patient model is preferably calculated without using a depth camera. The personalized patient model can typically be used particularly flexibly since it includes both internal and external information on the patient. Preferably, the personalized patient model provides a three-dimensional depiction of the entire body of the patient, in particular the body cavity and the organ.

One embodiment provides that the at least one metadata category comprises at least one entry from the following list:
the patient's weight,
the patient's height, and/or
the patient's gender.

The patient's weight corresponds for example to the body weight and the height of the patient in particular to the body height. The patient's gender is typically male or female. The use of this metadata is particularly advantageous because patient metadata is usually always available and simple to acquire. Alternatively or additionally, the at least one metadata category can comprise the angulation of an extremity of the patient.

The angulation of the extremity can, for example, describe that the extremity is at head height or alternatively extended along the patient's upper body. The angulation of the extremity is in particular measurable and/or dependent upon the imaging examination or a respective scan protocol.

Typically, during computed tomography examinations of the patient's upper body, the arms are extended above the head. In a particularly preferred embodiment, the angulation of the extremity can be acquired automatically, for example via an optical camera or depth camera. Typically, the external surface model of the patient, the internal anatomical model of the patient and/or the organ model of the patient is dependent on the angulation of the extremity.

One embodiment provides that, during the ascertainment of the external surface model of the patient, the patient's pose is taken into account. The patient's pose can, for example, describe a standing, lying or sitting posture. For example, the patient's pose can be taken into account during the ascertainment of the external surface model such that the external surface model has a standing, lying or sitting posture. In certain cases, the patient's pose can be such that the extremities of the patient are folded and/or extended and/or bent. In other words, the patient's pose is in particular dependent upon the angulation of the extremity of the patient. Taking the patient's pose into account can advantageously enable the external surface model, in particular the personalized patient model, of the patient to be matched to the respective positioning and/or posture of the patient.

One embodiment provides that the ascertainment of the external surface model of the patient includes the use of an external deformation model, wherein the external deformation model is matched to the patient's pose. The external deformation model in particular comprises at least one mathematical transform. The use of the external deformation model in particular includes the application of the external deformation model to an external surface model from a surface model database so that the external surface model is adapted to the respective patient. Herein, the application of the external deformation model in particular includes the adaptation of a pose of the external surface model to an actual patient pose.

For example, a standing external surface model can be transformed into a lying external surface model by using the external deformation model. The external deformation model in particular enables the external surface model to be deformed in accordance with the posture and/or positioning of the patient. For example, the external deformation model can be used to calculate the personalized patient model, in particular the surface model, for a patient lying on the stomach on a patient bench. In a further example, the external deformation model enables the ascertainment of the surface model of the patient, wherein the surface model has, for example, a sitting posture with extended extremities. The external deformation model can, for example, bend an extended arm and vice versa.

One embodiment provides that the external deformation model is matched to the physical forces and the physical forces influence the patient's pose. The physical forces describe, for example, a gravitational force, a locally prevailing gravitational field and/or inertia effects acting on the patient. Typically, the external deformation model is dependent upon the alignment of the patient's pose relative to a direction vector of the physical forces. The physical forces can, for example, be determined by the shape of the patient bench if, for example, the patient is wider than the bearing area of the patient bench. The physical forces are in particular different from 0 when the external deformation model describes the transformation from a standing posture to a sitting posture. The physical forces in particular influence the pose such that, for example, the stomach of an obese patient is depicted differently in standing or lying poses.

One embodiment provides that the ascertainment of the external surface model of the patient and the internal anatomical model of the patient is performed using a surface model database comprising external surface models, wherein surface-model-related metadata is assigned to each external surface model, and using a medical image database comprising medical image datasets, wherein medical metadata is assigned to each medical image dataset, wherein the surface-model-related metadata and the medical metadata is assigned to the at least one metadata category.

The external surface models in the surface model database are in particular generated during an external measurement of a plurality of training subjects. Typically, the plurality of training subjects is acquired in a standing or sitting pose via a depth camera or optical cameras for three-dimensional mapping of the plurality of training subjects. In addition, usually, the surface-model-related metadata is assigned to the three-dimensional mapping, wherein the surface-model-related metadata describe the respective training subject. In particular the external surface models are calculated from the three-dimensional mapping of the plurality of training subjects, wherein the surface-model-related metadata is assigned accordingly. The surface model database can, for example, be compiled by the clothing industry. Alternatively or additionally, the surface model database can comprise external surface models, which were, for example, acquired during radiation protection examinations. Radiation protection examinations are usually performed in a standing pose.

The medical image datasets in the medical image database are in particular generated during imaging examinations of training subjects via a medical imaging device. Typically, the medical image database is available at the site where the imaging examinations are performed or where the medical image datasets acquired during the imaging examinations are processed. The medical image database can, for example, correspond to a radiology information system (RIS) or an image archiving system (PACS, picture archiving and communication system). The medical image dataset has a pose of the respective training subject appropriate for the type of imaging examination.

Typically, the medical image datasets for computed tomography or magnetic resonance imaging examinations have a lying posture or pose, while, for example, the medical image datasets for an X-ray-based mammography examination can comprise the standing pose. The medical image datasets can in particular be derived from any medical imaging device. The medical image datasets preferably form an anatomy, a structure and/or a morphology of the training subject examined.

The internal anatomical model is in particular based on mapping of the structure, morphology and/or anatomy in the medical image datasets. In particular, the internal anatomical models can be calculated from the medical image datasets can. Typically, the medical metadata of the respective training subject examined is assigned to each medical image dataset of the respective medical imaging device. Usually, the DICOM format is used for the medical image datasets in order to link a respective item of image information to the corresponding medical metadata. Typically, more external surface models are available than medical image datasets.

Usually, it is only in rare cases that medical image datasets have a map of the entire body of the training subject. In contrast, external surface models typically comprise a map of the entire body. Medical datasets typically comprise a segment of the entire body, for example the legs of the training subject and/or the thorax of the training subject. It is preferably possible to calculate an external medical surface model, at least in segments, from the medical image datasets, in particular when the medical image datasets comprise a surface, preferably a skin.

The fact that the patient metadata, the surface-model-related metadata and the medical metadata are assigned to the at least one metadata category in particular means that the patient metadata, the surface-model-related metadata and the medical metadata preferably comprise a common feature and/or common aspect. Therefore, the at least one metadata category is in particular a comparable parameter, wherein the patient metadata, the surface-model-related metadata and the medical metadata comprise the comparable parameter. It is conceivable that the patient metadata comprises further metadata categories, which typically do not comprise the surface-model-related metadata and/or the medical metadata in each case and vice versa. The at least one metadata category in particular forms a connection between the medical image datasets and the external surface models.

One embodiment provides that the ascertainment of the external surface model of the patient is performed using the surface model database and the medical image database and wherein the ascertainment of the internal anatomical model of the patient is exclusively performed using the medical image database. Preferably, the medical image datasets in the medical image database comprise the pose or at least one similar pose compared to the external surface models in the surface model database. In particular when the medical image datasets and the external surface models comprise the same pose, the application of the external deformation model can be superfluous. In this case, preferably only the external surface model is ascertained and typically the external deformation model is applied to neither the external surface model nor the internal anatomical model. In other words, in particular the calculation of the external deformation model is performed using the surface model database and the medical image database.

One embodiment provides that the ascertainment of the internal anatomical model of the patient is performed using the medical image database, which comprises the medical image datasets, wherein the medical metadata is assigned to each medical image dataset, wherein the medical metadata is assigned to the at least one metadata category, and a selection of at least one medical image dataset from the medical image datasets in the medical image database is performed in accordance with the patient metadata and an ascertainment of the body cavity of the internal anatomical model of the patient is performed using the at least one medical image dataset. The selection of the at least one medical image dataset can include learning a first relationship between the at least one metadata category and the medical image datasets to which the medical metadata is assigned. In accordance with the first relationship, preferably the at least one medical image dataset is selected in accordance with the patient metadata. The at least one medical image dataset is advantageously selected to match the patient as closely as possible since the patient metadata is used as the input parameters for the selection. It is possible for the at least one medical image dataset to be calculated from a plurality of medical image datasets in accordance with the patient metadata, for example by averaging or similar mathematical methods.

The learning of the first relationship can comprise a first regression analysis. Generally speaking, regression analysis is a statistical method for modeling relationships between a dependent variable and an independent variable. The relationship between the variables is usually described in regression procedures.

Regression analysis typically solves a regression problem. Usually, different methods are used to solve the regression problem, in particular linear or multi-linear regression, a support vector machine (SVM), a kernel SVM, and/or deep-learning methods via artificial neural networks. Regression analysis can be used, preferably using input parameters, to ascertain or estimate output data. In this way, it is also possible for the ascertainment of the external surface model of the patient and the internal anatomical model of the patient to comprise the application of regression analysis, wherein the patient metadata is used as the input parameters.

The ascertainment of the organ model of the patient in particular comprises a further application of a regression analysis, wherein the patient metadata is used as the input parameters. In these cases, the ascertainment in particular corresponds to the provision of the external surface model of the patient and the internal anatomical model of the patient and the organ model of the patient as output data of the respective regression analysis.

One embodiment provides that the ascertainment of the external surface model of the patient is performed using the surface model database comprising the external surface models, wherein the surface-model-related metadata is assigned to each external surface model, wherein the surface-model-related metadata is assigned to the at least one metadata category and comprises: selection of an estimated external surface model from the external surface models in the surface model database in accordance with the patient metadata, calculation of an external deformation model using the estimated external surface model, and application of the external deformation model to the estimated external surface model, wherein the external surface model of the patient is generated.

The selection of the estimated external surface model can include learning a second relationship between the at least one metadata category and the external surface models to which the surface-model-related metadata is assigned. Usually, the learning of the second relationship comprises a second regression analysis. The second relationship is preferably used as the basis for the selection of the estimated external surface model in accordance with the patient metadata. The estimated external surface model is advantageously selected to match the patient as closely as possible since the patient metadata is used as the input parameters for the selection. It is in particular possible for the estimated external surface model to be calculated from a plurality of similar external surface models in accordance with the patient metadata, for example by way of averaging or similar mathematical methods.

The estimated external surface model is used as the basis for matching the external deformation model in particular to the patient's pose. The estimated external surface model is in particular a first input parameter for the calculation of the external deformation model. When the external deformation model is applied to the estimated external surface model, the estimated external surface model is, for example, transformed according to the patient's pose. For example, the estimated external surface model comprises a standing pose while the external surface model of the patient in particular comprises a lying pose. The estimated external surface model and the external surface model of the patient in particular differ in the application of the external deformation model.

Alternatively or additionally, the external deformation model can be applied to the internal anatomical model of the patient. In this case, for example, the body cavity, in particular a position and/or a volume of the body cavity, are adapted in accordance with the external surface model. The relationship between the external surface model of the patient and the organ model of the patient is adapted accordingly. This is in particular advantageous when the external deformation model is determined by the angulation of the extremity of the patient. For example, the position of the lung relative to the skin shifts when the external deformation model describes the transformation from a patient's arms extended above the head to a patient's arms lying crossed on the stomach.

One embodiment provides that the calculation of the external deformation model is performed using the medical image database comprising the medical image datasets, wherein the medical metadata is assigned to each medical image dataset, wherein the medical metadata is assigned to the at least one metadata category and comprises:

selection of the at least one medical image dataset from the medical image datasets in the medical image database in accordance with the patient metadata, and registration of the estimated external surface model and the at least one medical image dataset.

The selection of the at least one medical image dataset can, for example, be performed in accordance with the first relationship or using first regression analysis. In principle, it is conceivable that further regression analysis is performed for learning a further relationship between the at least one metadata category and the medical image datasets, which in particular comprise the medical metadata. The patient metadata is in this case input parameters for further regression analysis and output data in particular comprises the at least one medical image dataset. Usually, the registration is performed in accordance with rigid registration. In particular, the external deformation model can be calculated in accordance with rigid registration.

One embodiment provides that, before registration of the estimated external deformation model, the at least one medical image dataset is segmented in accordance with a first segmentation protocol, and/or that the body cavity of the internal anatomical model of the patient is ascertained by segmentation of the at least one medical image dataset in accordance with a second segmentation protocol.

The first segmentation protocol can in particular be embodied in accordance with the skin and/or a surface of the respective patient. In other words, during segmentation in accordance with the first segmentation protocol, in particular the skin is ascertained in the at least one medical image dataset. The skin is in particular mapped in the morphology, in the structure and/or the anatomy in the medical image datasets. The first segmented at least one medical image dataset preferably corresponds to the external medical surface model. The external medical surface model is preferably used instead of the at least one medical image dataset during registration with the estimated external surface model. The external medical surface model is in particular a second input parameter for the calculation of the external deformation model.

The second segmentation protocol in particular enables the ascertainment of the anatomical enclosure or the convex enclosure, for example around an organ in the at least one medical image dataset. The morphology, the structure and/or the anatomy in the medical image datasets in particular comprise the anatomical enclosure, typically the body cavity, and in particular the organ included in the anatomical enclosure. The body cavity in particular corresponds to the anatomical enclosure or the convex enclosure. Two typical examples of an anatomical enclosure are in particular the thoracic cavity (Cavitas thoracis) and the abdominal cavity (Cavitas abdominalis).

One embodiment provides that, additionally to the body cavity, the internal anatomical model comprises a further body cavity, wherein the body cavity comprises the patient's thorax and the further body cavity comprises the patient's abdomen and wherein, during the ascertainment of the organ model of the patient, a distance between the body cavity 'thorax' and the further body cavity 'abdomen' is minimized. The body cavity 'thorax' in particular corresponds to the thoracic cavity and the further body cavity 'abdomen' in particular corresponds to the abdominal cavity. The organ can in particular be arranged inside the body cavity or the further body cavity.

The plurality of organs can in each case in particular be arranged inside the body cavity or the further body cavity. For example, the body cavity 'thorax' can comprise the patient's heart and/or lung while the further body cavity 'abdomen' comprises the patient's liver. In other words, the body cavity 'thorax' forms a first convex enclosure around the heart or the lung and the further body cavity 'abdomen' forms a second convex enclosure around the liver.

Typically, an intersection between the body cavity and the further body cavity is empty. In this case, in particular the distance between the heart and the liver or between the lung and the liver can be minimized. The minimization can, for example, be specified in standard medical literature. The organ model can comprise the body cavity and the further body cavity, in particular the body cavity 'thorax' and the further body cavity 'abdomen'. For example, instead of being minimized during the ascertainment of the internal anatomical model, the distance between the body cavity 'thorax' and the body cavity 'abdomen' can be minimized during the ascertainment of the organ model.

One embodiment provides that the ascertainment of the organ model of the patient is performed using the medical image database, which comprises the medical image datasets, wherein the medical metadata is assigned to each medical image dataset, wherein the medical metadata is assigned to the at least one metadata category. Typically, exclusively the medical image database and the patient metadata is used for the ascertainment of the organ model of the patient. Usually, the medical image database for the ascertainment of the organ model of the patient can in particular correspond to the medical image database for the ascertainment of the surface model of the patient and the internal anatomical model of the patient. In other words, the medical image database can be used for the ascertainment of the organ model of the patient and for the ascertainment of the surface model of the patient and the internal anatomical model of the patient.

One embodiment provides that the ascertainment of the organ model comprises:

selection of the at least one medical image dataset from the medical image datasets in the medical image database in accordance with the patient metadata, segmentation of the at least one medical image dataset in accordance with a third segmentation protocol, calculation of at least one internal deformation model using the internal anatomical model of the patient and the at least one segmented medical image dataset, application of the at least one internal deformation model to the at least one segmented medical image dataset and classification of the internal anatomical model of the patient in accordance with the at least one deformed medical image dataset, wherein the organ model is generated.

The selection of the at least one medical image dataset can preferably be performed in accordance with the first relationship or using first regression analysis. In principle, it is conceivable that a further regression analysis is performed for a learning a further relationship between the at least one metadata category and the medical image datasets, which in particular comprise the medical metadata. In this case, the at least one medical image dataset can be selected using further regression analysis.

The third segmentation protocol in particular enables the ascertainment of the anatomical enclosure or the convex enclosure, in particular around the organ in the at least one medical image dataset. Preferably, the segmented at least one medical image dataset comprises the anatomical enclosure around the organ and the organ itself. In particular when, additionally to the organ, a further organ is mapped in the at least one medical image dataset and the anatomical enclosure comprises the organ and the further organ, the segmented at least one medical image dataset comprises the anatomical enclosure around the organ and the further organ and the organ and the further organ. Depending upon the position of the organ and the further organ relative to one another, the anatomical enclosure can comprise the organ, the further organ and a filling space, wherein a sum total of the organ, the further organ and the filling space produces a volume of the anatomical enclosure. The anatomical enclosure, the convex enclosure and the body cavity usually correspond to one another. Typically, the third segmentation protocol can correspond to the second segmentation protocol.

The calculation of the at least one internal deformation model in particular comprises non-rigid registration of the internal anatomical model of the patient and the at least one segmented medical image dataset. For example, before non-rigid registration, the mathematically modeled depiction of the internal anatomical model of the patient and the mathematically modeled depiction of the at least one medical image dataset can be converted into the respective image-based depiction. Typically, rigid and/or non-rigid registration in performed in an image-based manner. Rigid registration in particular includes rotation and translation, while non-rigid registration in particular comprises elastic transformation. For example, it is possible to set landmarks for rigid and/or non-rigid registration, in particular in the at least one medical image datasets, wherein the landmarks can simplify registration.

The application of the at least one internal deformation model in particular causes the at least one medical image dataset to be deformed. When the at least one medical image dataset comprises the body cavity and, for example, the organ inside the body cavity, preferably the body cavity and the organ are deformed in accordance with the at least one internal deformation model.

Typically, before classification, the internal anatomical model does not comprise the organ but exclusively the body cavity, wherein the organ should be embedded. The deformed and in particular segmented at least one medical image dataset comprises preferably the organ, for example additionally the further organ, and the body cavity. Usually, after the application of the at least one internal deformation model, the body cavity of the internal anatomical model and the body cavity, in particular the anatomical enclosure around the organ and the further organ, in the at least one medical image dataset are congruent. Preferably, the classification of the internal anatomical model of the patient can include a voxel-based check as to whether the respective voxel in the at least one medical image dataset comprises the organ. If the respective voxel comprises the organ, a corresponding voxel of the internal anatomical model of the patient is also classified as the organ. After classification, the internal anatomical model of the patient preferably comprises the organ, when the deformed at least one medical image dataset also comprises the organ. As a result, in particular the organ model is generated.

The computing unit according to an embodiment of the invention for the calculation of the personalized patient model comprises a computing module. The computing unit is in particular embodied to calculate the personalized patient model. The computing module in particular comprises a processor and a working memory, wherein the processor can preferably carry out the method steps for calculating the personalized patient model. The computing unit can additionally comprise an input device and the screen, wherein, for example, the user can acquire the patient metadata via the input device and in particular display this on the screen. Preferably, the screen can display the personalized patient model and/or stored it on a hard disk of the computing unit.

The computing unit can, for example, transfer the personalized patient model and/or the patient metadata via a suitable interface to a computer network or to the medical imaging device or to an external memory unit and/or retrieve them therefrom. The computing unit is preferably connected to the computer network, in particular the surface model database and/or the medical image database. Alternatively or additionally, the computing unit or the external memory unit connected to the computing unit can comprise the surface model database and/or the medical image database. The computing unit can in particular comprise the model generator and/or the organ-model generator.

The computer program product according to an embodiment of the invention, which can be loaded directly into a memory of a programmable computing unit, comprises program code segments for carrying out a method of an embodiment, when the computer program product is executed in the computing unit. The computer program product can be a computer program or comprise a computer program. This enables the method according to an embodiment of the invention to be carried out in a rapid, identically repeatable and robust manner.

The computer program product is preferably configured such that it can carry out the methods steps according to an embodiment of the invention via the computing unit. The computer program product is, for example, stored on a non-transitory computer-readable medium or held in the computer network or on a server from where it can be loaded into the processor of the computing unit. Furthermore, control information of the computer program product can be stored on an electronically readable data carrier. The control information of the electronically readable data carriers can be embodied such it carries out a method according to the invention that when the data carrier is used in the computing unit. Thus, the computer program product can also depict the electronically readable data carrier.

Examples of electronically readable data carriers are a DVD, a magnetic tape, a hard disk or a USB stick on which electronically readable control information, which in particular correspond to program code segments are stored. When this control information is read from the data carrier and stored in the computing unit, all the inventive embodiments of the above-described method can be performed. For example, an embodiment of the invention can also be based on the computer-readable medium and/or the electronically readable data carrier. The computer program product can in particular comprise the model generator and/or the organ-model generator.

Figure 1:
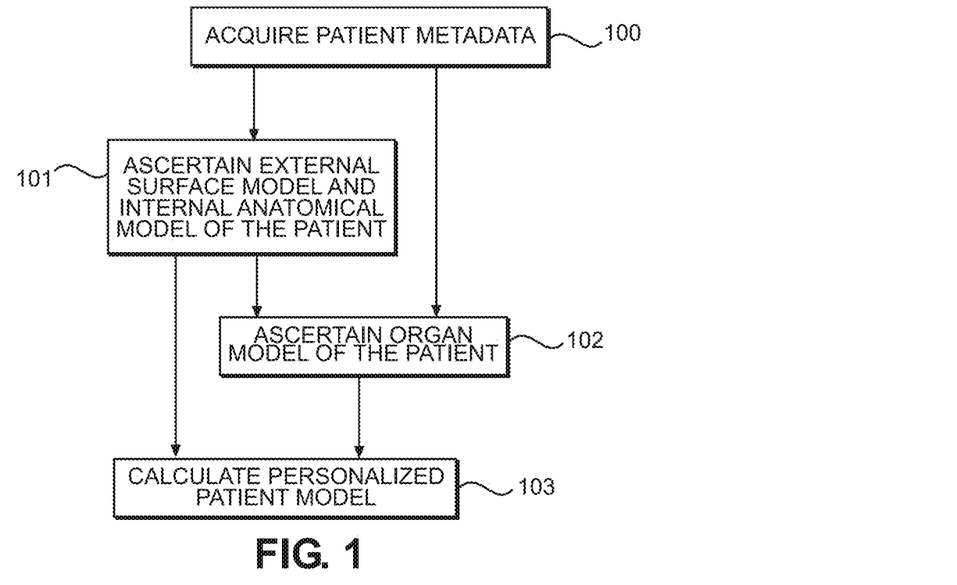
FIG. 1 shows a method in a first example embodiment.

FIG. 1 shows a method for calculating a personalized patient model in a first example embodiment. The personalized patient model comprises an external surface model of a patient and an organ model of the patient. The method for the calculation of the personalized patient model comprises the method steps 100 to 103.

Method step 100 is directed to an acquisition of patient metadata, wherein the metadata is assigned to at least one metadata category.

Method step 101 is directed to an ascertainment of the external surface model of the patient and an internal anatomical model of the patient, wherein the internal anatomical model comprises a body cavity of the patient, using the patient metadata.

Method step 102 is directed to an ascertainment of the organ model of the patient using the patient metadata and the internal anatomical model of the patient.

Method step 103 is directed to a calculation of the personalized patient model, wherein the external surface model of the patient and the organ model of the patient are combined.

The description below of the following example embodiments is substantially restricted to the differences from the example embodiment in FIG. 1, wherein reference is made to the description of the example embodiment in FIG. 1 with respect to method steps that remain the same. Method steps that substantially remain the same are in principle provided with the same reference characters.

Figure 2:
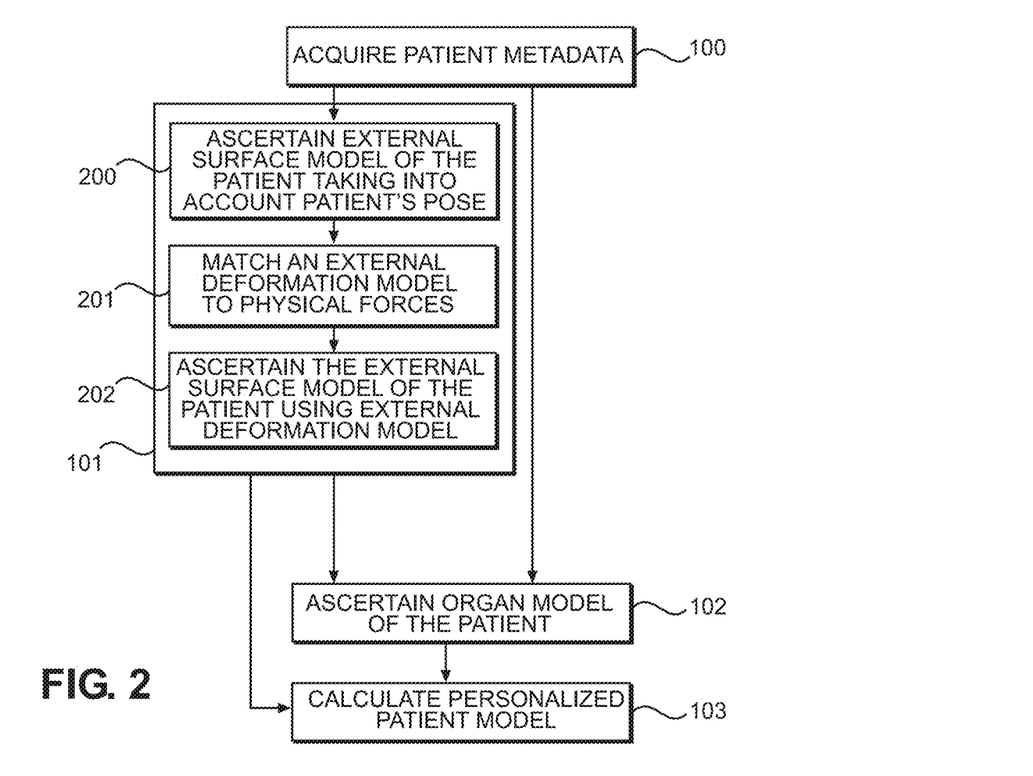
FIG. 2 shows a method in a second example embodiment.

FIG. 2 shows the method for the calculation of the personalized patient model in a second example embodiment. In this example embodiment, the at least one metadata category comprises the patient's weight, the patient's height and the patient's gender.

Method step 200 is directed to the fact that the patient's pose is taken into account during the ascertainment of the external surface model of the patient.

Method step 201 is directed to the fact that an external deformation model is matched to physical forces and wherein the physical forces influence the patient's pose.

Method step 202 is directed to the fact that the ascertainment of the external surface model of the patient includes a use of the external deformation model, wherein the external deformation model is matched to the patient's pose.

Figure 3:
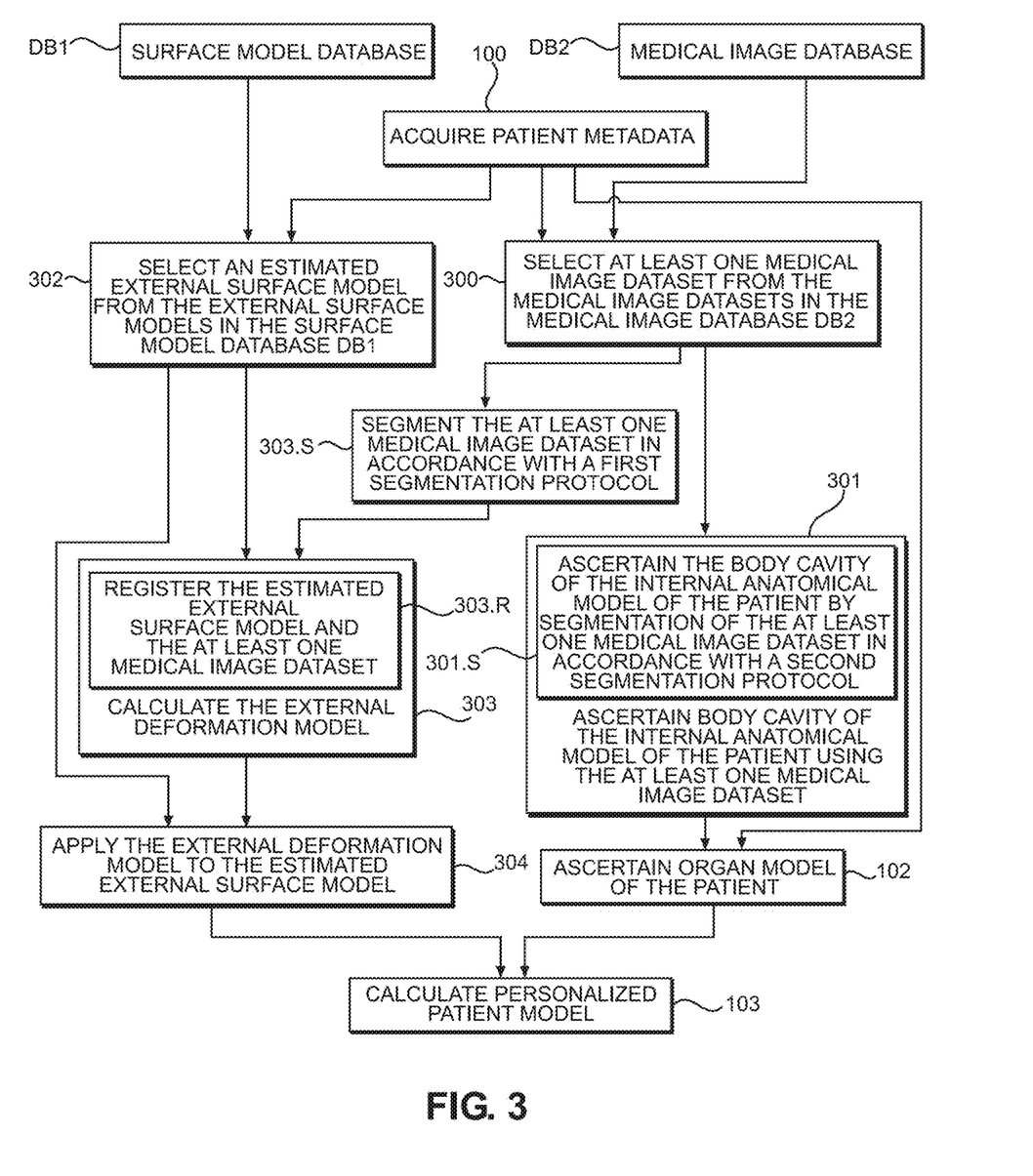
FIG. 3 shows a method in a third example embodiment.

FIG. 3 shows the method for the calculation of the personalized patient model in a third example embodiment.

The ascertainment of the external surface model of the patient and the internal anatomical model of the patient is performed using a surface model database DB1 comprising external surface models, wherein surface-model-related metadata is assigned to each external surface model, and using a medical image database DB2 comprising medical image datasets, wherein medical metadata is assigned to each medical image dataset, wherein the surface-model-related metadata and the medical metadata is assigned to the at least one metadata category. In this example embodiment, the ascertainment of the external surface model of the patient is performed using the surface model DB1 and the medical image database DB2, wherein the ascertainment of the internal anatomical model of the patient is exclusively performed using the medical image database DB2.

The ascertainment of the internal anatomical model of the patient includes the following method steps 300, 301.S and 301.

The method step 300 is directed to a selection of at least one medical image dataset from the medical image datasets in the medical image database DB2 in accordance with the patient metadata.

The method step 301.S is directed to the fact that the body cavity of the internal anatomical model of the patient is ascertained by segmentation of the at least one medical image dataset in accordance with a second segmentation protocol. The second segmentation protocol is embodied for the segmentation of an anatomical enclosure or a convex enclosure, in particular the body cavity, in the at least one medical image dataset.

The method step 301 is directed to an ascertainment of the body cavity of the internal anatomical model of the patient using the at least one medical image dataset.

Method step 302 is directed to a selection of an estimated external surface model from the external surface models in the surface model database DB1 in accordance with the patient metadata.

Method step 303 is directed to the calculation of the external deformation model using the estimated external surface model, wherein the calculation of the external deformation model includes the method step 300 and the following method steps 303.S and 303.R.

The method step 303.S is directed to the fact that, before registration of the estimated external deformation model, the at least one medical image dataset is segmented in accordance with a first segmentation protocol. The first segmentation protocol is embodied for the segmentation of a surface, in particular a skin, in the at least one medical image dataset.

The method step 303.R is directed to registration of the estimated external surface model and the at least one medical image dataset.

Method step 304 is directed to an application of the external deformation model to the estimated external surface model, wherein the external surface model of the patient is generated.

Figure 4:
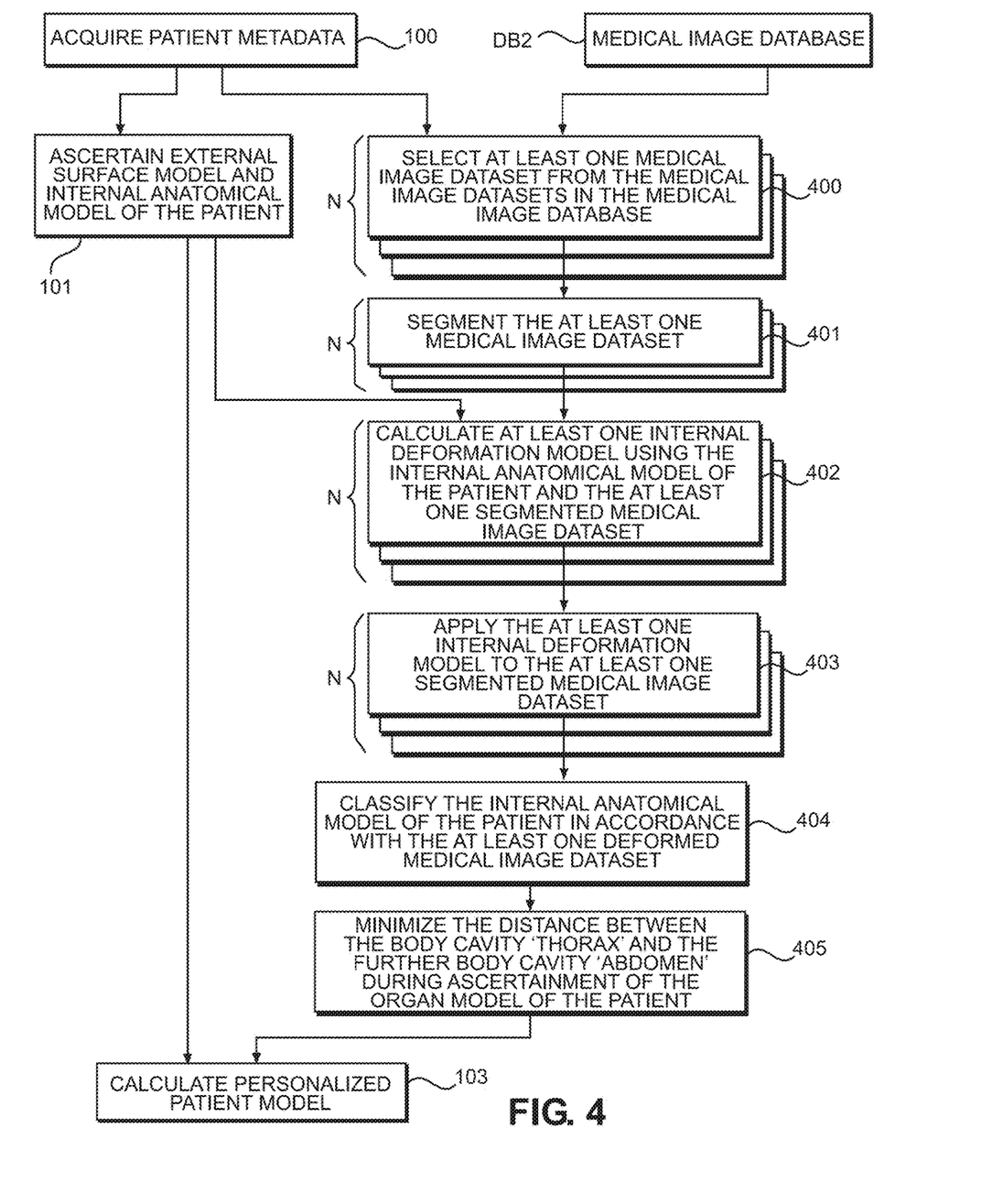
FIG. 4 shows a method in a fourth example embodiment and
FIG. 5 shows a personalized patient model.

FIG. 4 shows the method for the calculation of the personalized patient model in a fourth example embodiment.

The ascertainment of the organ model of the patient is performed using the medical image database DB2, which comprises the medical image datasets, wherein the medical metadata is assigned to each medical image dataset, wherein the medical metadata is assigned to the at least one metadata category.

The ascertainment of the organ model includes the following method steps 400 to 404.

The method step 400 is directed to a selection of at least one medical image dataset from the medical image datasets in the medical image database in accordance with the patient metadata. In this example embodiment, a number N greater than 1 of medical image datasets is selected. This is in particular advantageous for the classification of the internal anatomical model of the patient. Usually, the N most similar medical image datasets are selected from the medical image datasets in the medical image database.

The method step 401 is directed to a segmentation of the at least one medical image dataset in accordance with a third segmentation protocol. In this method step, the segmentation performed N-times in the N most similar medical image datasets.

The method step 402 is directed to a calculation of at least one internal deformation model using the internal anatomical model of the patient and the at least one segmented medical image dataset. In this method step, N internal deformation models are calculated separately using the internal anatomical model of the patient and the N most similar medical image datasets.

The method step 403 is directed to an application of the at least one internal deformation model to the at least one segmented medical image dataset. In this method step, the N internal deformation models are applied to the respective N most similar medical image datasets.

The method step 404 is directed to a classification of the internal anatomical model of the patient in accordance with the at least one deformed medical image dataset, wherein the organ model is generated. The classification is performed in accordance with a majority decision as to whether or not an examined voxel comprises an organ. Usually, the more similar medical image datasets selected, i.e. the higher N is, the more robust the classification. The decisive factor for the classification is in particular a measure of the similarity of the at least one medical image dataset. The measure for the similarity in particular correlates with a quality of the personalized patient model. The similarity of the medical image datasets is, for example, determined by way of a nearest-neighbor classification (k-nearest neighbor). Preferably, N medical image datasets with a high degree of similarity are selected.

Method step 405 is directed to the fact that, additionally to the body cavity, the internal anatomical model comprises a further body cavity, wherein the body cavity comprises the patient's thorax and the further body cavity comprises the patient's abdomen and wherein, during the ascertainment of the organ model of the patient, the distance between the body cavity 'thorax' and the further body cavity 'abdomen' is minimized.

Figure 5:
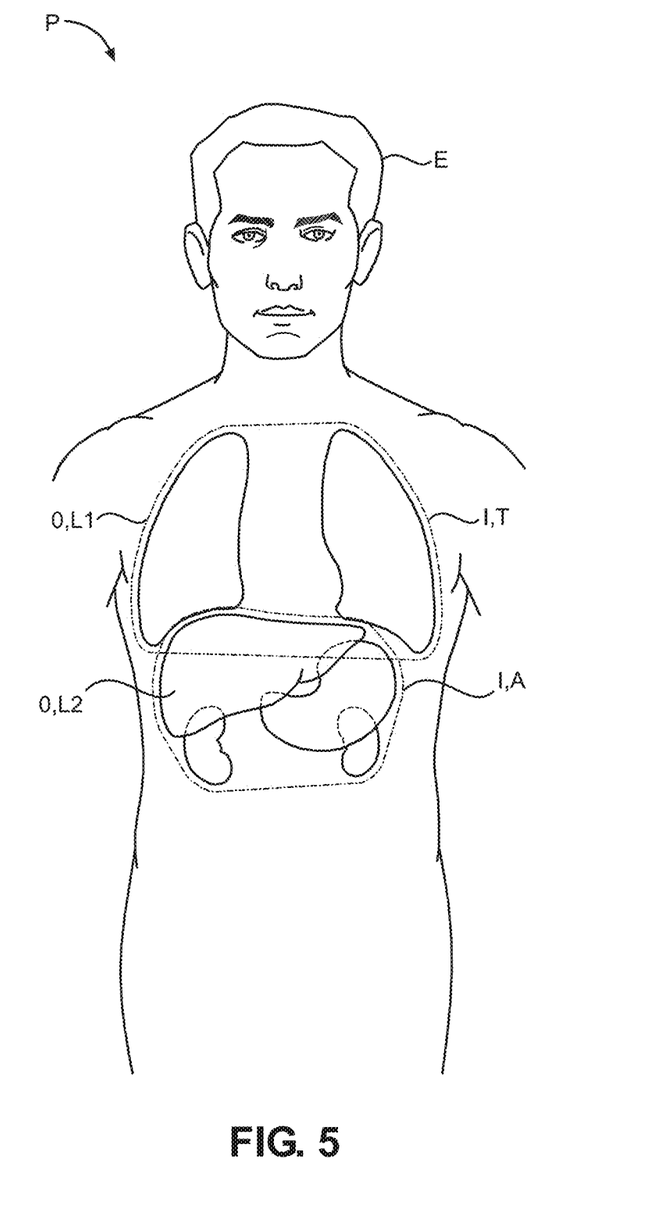

FIG. 5 shows the personalized patient model in one possible embodiment. FIG. 5 in particular shows an abstraction of the personalized patient model. Obviously further embodiments of the personalized patient model in addition to the embodiment shown in FIG. 5 are also conceivable. The personalized patient model P comprises the external surface model E of the patient, the internal anatomical model I of the patient and the organ model O of the patient. The external surface model E of the patient shows a segment of an upper body of the patient and demarcates the patient's skin. The internal anatomical model I of the patient comprises the body cavity 'thorax' T and the further body cavity 'abdomen' A. The organ model O of the patient is arranged inside the internal anatomical model I. The organ model O of the patient comprises a plurality of organs, in this case a lung L1 of the patient and the patient's liver L2. The body cavity 'thorax' T comprises a lung L1 of the patient and the further body cavity 'abdomen' A comprises the patient's liver L2. An intersection between the body cavity 'thorax' T and the further body cavity 'abdomen' A is empty, although in the depiction of the personalized patient model P in FIG. 5 a superimposition of the body cavity 'thorax' T and the further body cavity 'abdomen' A is indicated.

Although the invention was illustrated and described in more detail by the preferred example embodiments, the invention is not restricted by the disclosed examples and other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for calculating a personalized patient model including an external surface model of a patient and an organ model of the patient, the method comprising:
   acquiring metadata of the patient, the metadata of the patient being assigned to at least one metadata category;
   ascertaining, based on the metadata of the patient, the external surface model of the patient and an internal anatomical model of the patient, the internal anatomical model of the patient including a body cavity of the patient;
   obtaining the organ model of the patient using the metadata of the patient and the internal anatomical model of the patient; and
   calculating the personalized patient model, wherein the external surface model of the patient and the organ model of the patient are combined; wherein
      the ascertaining of the external surface model of the patient is performed using a surface model database including external surface models and using a medical image database including medical image datasets,
      the ascertaining of the internal anatomical model of the patient is performed using only the medical image database from among the surface model database and the medical image database, and
      the acquiring, the ascertaining, the obtaining and the calculating are performed without using a depth camera to provide depth information of the patient.

2. The method of claim 1, wherein the at least one metadata category comprises at least one of:
   a weight of the patient,
   a height of the patient, or
   a gender of the patient.

3. The method of claim 1, wherein a pose of the patient is taken into account during ascertaining the external surface model of the patient.

4. The method of claim 3, wherein
   the ascertaining the external surface model of the patient is based on an external deformation model, and
   the external deformation model is matched to the pose of the patient.

5. The method of claim 4, wherein
   the external deformation model is matched to physical forces, and
   the physical forces influence the pose of the patient.

6. The method of claim 1, wherein
   surface-model-related metadata is assigned to each of the external surface models,
   medical metadata is assigned to each of the medical image datasets, and
   the surface-model-related metadata and the medical metadata are assigned to the at least one metadata category.

7. The method of claim 1, wherein the ascertaining the internal anatomical model of the patient comprises:
   selecting at least one medical image dataset from among the medical image datasets in the medical image database based on the metadata of the patient, and
   ascertaining a body cavity of the internal anatomical model of the patient using the at least one medical image dataset, wherein
      medical metadata is assigned to each of the medical image datasets, and
      the medical metadata is assigned to the at least one metadata category.

8. The method of claim 1, wherein the ascertaining the external surface model of the patient comprises:
   selecting an estimated external surface model from the external surface models in the surface model database based on the metadata of the patient,
   calculating an external deformation model using the estimated external surface model, and
   applying the external deformation model to the estimated external surface model to generate the external surface model of the patient, wherein
      surface-model-related metadata is assigned to each of the external surface models, and
      the surface-model-related metadata is assigned to the at least one metadata category.

9. The method of claim 8, wherein the calculating the external deformation model comprises:
   selecting at least one medical image dataset from the medical image datasets in the medical image database based on the metadata of the patient, and
   registering the estimated external surface model and the at least one medical image dataset, wherein
      medical metadata is assigned to each of the medical image datasets, and
      the medical metadata is assigned to the at least one metadata category.

10. The method of claim 9, further comprising at least one of
   segmenting, before registering of the estimated external surface model, the at least one medical image dataset in accordance with a first segmentation protocol, or
   ascertaining the body cavity of the internal anatomical model of the patient by segmenting the at least one medical image dataset in accordance with a second segmentation protocol.

11. The method of claim 1, wherein
   the internal anatomical model includes a further body cavity,
   the body cavity includes a thorax of the patient and the further body cavity includes an abdomen of the patient, and
   the method further includes minimizing a distance between the thorax and the abdomen during the obtaining the organ model of the patient.

12. The method of claim 1, wherein
   the obtaining the organ model of the patient is performed using the medical image database,
   medical metadata is assigned to each of the medical image datasets, and
   the medical metadata is assigned to the at least one metadata category.

13. The method of claim 12, wherein the obtaining the organ model comprises:
- selecting at least one medical image dataset from the medical image datasets in accordance with the metadata of the patient,
- segmenting the at least one medical image dataset,
- calculating at least one internal deformation model using the internal anatomical model of the patient and the segmented at least one medical image dataset,
- applying the at least one internal deformation model to the segmented at least one medical image dataset to produce at least one deformed medical image dataset, and
- classifying the internal anatomical model of the patient in accordance with the at least one deformed medical image dataset.

14. A computing unit for calculating a personalized patient model of a patient, the computing unit comprising:
- a computing module embodied to, without using a depth camera to provide depth information of the patient, perform at least
  - acquiring metadata of the patient, the metadata of the patient being assigned to at least one metadata category,
  - ascertaining, based on the metadata of the patient, an external surface model of the patient and an internal anatomical model of the patient, the internal anatomical model including a body cavity of the patient,
  - obtaining an organ model of the patient based on the metadata of the patient and the internal anatomical model of the patient; and
  - calculating the personalized patient model, wherein the external surface model of the patient and the organ model of the patient are combined, wherein
    - the external surface model of the patient is ascertained using a surface model database including external surface models and using a medical image database including medical image datasets,
    - the internal anatomical model of the patient is ascertained using only the medical image database from among the surface model database and the medical image database.

15. The computing unit of claim 14, wherein the computing module includes a processor and a memory.

16. The computing unit of claim 15, further comprising:
- an input device; and
- a display screen to display the metadata of the patient.

17. A non-transitory computer readable medium storing program code segments for carrying out the method of claim 1 upon the program code segments being executed in a computing unit.

18. The method of claim 2, wherein a pose of the patient is taken into account during ascertaining the external surface model of the patient.

19. The method of claim 18, wherein
- the ascertaining the external surface model of the patient includes using an external deformation model, and
- the external deformation model is matched to the pose of the patient.

20. The method of claim 19, wherein
- the external deformation model is matched to physical forces, and
- the physical forces influence the pose of the patient.

21. A device for calculating a personalized patient model of a patient, the device comprising:
- a memory storing computer-readable instructions; and
- at least one processor configured to execute the computer-readable instructions to cause the device to, without using a depth camera to provide depth information of the patient, perform
  - acquiring metadata of the patient, the metadata of the patient being assigned to at least one metadata category,
  - ascertaining, based on the metadata of the patient, an external surface model of the patient and an internal anatomical model of the patient, the internal anatomical model of the patient including a body cavity of the patient,
  - obtaining an organ model of the patient using the metadata of the patient and the internal anatomical model of the patient, and
  - calculating the personalized patient model including the external surface model of the patient and the organ model of the patient combined; wherein
    - the external surface model of the patient is ascertained using a surface model database including external surface models and using a medical image database including medical image datasets, and
    - the internal anatomical model of the patient is ascertained using only the medical image database from among the surface model database and the medical image database.

* * * * *